(12) United States Patent
Opsal et al.

(10) Patent No.: US 7,050,162 B2
(45) Date of Patent: May 23, 2006

(54) OPTICAL METROLOGY TOOL HAVING IMPROVED CONTRAST

(75) Inventors: Jon Opsal, Livermore, CA (US); David Y. Wang, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 385 days.

(21) Appl. No.: 10/156,504

(22) Filed: May 28, 2002

(65) Prior Publication Data

US 2003/0133102 A1 Jul. 17, 2003

Related U.S. Application Data

(60) Provisional application No. 60/349,672, filed on Jan. 16, 2002.

(51) Int. Cl.
*G01N 21/00* (2006.01)

(52) U.S. Cl. .................. 356/237.1; 356/237.2; 356/237.5; 438/16

(58) Field of Classification Search .............. 356/237.1, 356/237.2, 237.5, 445; 438/16, 15
See application file for complete search history.

(56) References Cited

U.S. PATENT DOCUMENTS

| | | | | |
|---|---|---|---|---|
| 4,378,159 A | * | 3/1983 | Galbraith | 356/237.3 |
| 4,398,825 A | * | 8/1983 | Lewis | 356/426 |
| 4,790,659 A | | 12/1988 | Erman et al. | 356/369 |
| 5,166,752 A | | 11/1992 | Spanier et al. | 356/369 |
| 5,486,701 A | | 1/1996 | Norton et al. | 250/372 |
| 5,608,526 A | | 3/1997 | Piwonka-Corle et al. | 356/369 |
| 5,747,813 A | | 5/1998 | Norton et al. | 250/372 |
| 5,859,424 A | | 1/1999 | Norton et al. | 250/226 |
| 6,184,984 B1 | | 2/2001 | Lee et al. | 356/369 |
| 6,278,519 B1 | | 8/2001 | Rosencwaig et al. | 356/369 |
| 6,323,946 B1 | | 11/2001 | Norton | 356/327 |
| 6,556,361 B1 | * | 4/2003 | Smith et al. | 359/738 |
| 2002/0039184 A1 | | 4/2002 | Sandusky | 356/369 |

OTHER PUBLICATIONS

M. Born et al., "Principles of Optics," *Electromagnetic Theory of Propagation Interference and Diffraction of Light*, 6th Edition, 6th edition published 1980, Chapter X –entitled: "Interference and Diffraction with Partially Coherent Light," pp. cover, title page, copyright page, 491–555.

J.A. Zapien et al., "Real–time spectroscopic elipsometry from 1.5 to 6.5 eV," *Thin Solid Films*, vol. 364, No. 1,2,27 Mar. 2000, pp. cover 16–21.

H. El Rhaleb et al., "Beam size and collimation effects in spectroscopic ellipsometry of transparent films with optical thickness inhomogeneity," *Thin Solid Films*, vol. 228, 1996, pp. 125–131.

B. Drevillon et al., "Fast polarization modulated ellipsometer using a microprocessor system for digital fourier analysis," *Rev. Sci. Instrum.*, vol. 53, No. 7, Jul. 1982, pp. 969–977.

M. Erman et al., "Spatially resolved ellipsometry," *J. Appl. Phys.*, vol. 60, No. 3, Aug. 1, 1986, pp. 859–873.

(Continued)

*Primary Examiner*—Frank G. Font
*Assistant Examiner*—Roy M. Punnoose
(74) *Attorney, Agent, or Firm*—Stallman & Pollock LLP

(57) ABSTRACT

The subject invention relates to broadband optical metrology tools for performing measurements of patterned thin films on semiconductor integrated circuits. Particularly a family of optical designs for broadband optical systems wherein the ratio of illumination system to collection system numerical apertures is less than 1. System performance is enhanced through selection and control of the optical system partial coherence; this is accomplished through installation of beam-control apertures within the illumination and collection optical systems. The invention is broadly applicable to a large class of broadband optical wafer metrology techniques including spectrophotometry, spectroscopic reflectometry, spectroscopic ellipsometry and spectroscopic scatterometry.

28 Claims, 3 Drawing Sheets

OTHER PUBLICATIONS

K.K. Svitashev et al., "Use of a Convergent Light Beam for Ellipsometric Measurements," *Optika i Spektroskopiya,* vol. 30, No. Mar. 30, 1971, Translated in *Optics and Spectroscopy,* vol. 30, No. 3, Mar. 1971, pp. 288–291.

D.O. Barsukov et al., "Precision ellipsometry based on a focused light beam. Part 1, " *Opt. Spectrosc. (USSR),* vol. 64, No. 6, Jun. 1988, pp. 782–785.

B.D. Cahan et al., "High Speed Precision Automatic Ellipsometer," *Surface Science,* vol. 16, pp. 166–176.

R.H. Muller et al., "Use of Film–Formation Models for the Interpretation of Ellipsometer Observations," *Surface Science,* vol. 96, 1980, pp. 375–400.

\* cited by examiner

OPTICAL METROLOGY TOOL HAVING IMPROVED CONTRAST

PRIORITY CLAIM

The present application claims priority to U.S. Provisional Patent Application Serial No. 60/349,672, filed Jan. 16, 2002, which is incorporated herein by reference.

TECHNICAL FIELD

The subject invention relates to the field of optical metrology, particularly broadband optical metrology tools for performing measurements of patterned thin films on semiconductor integrated circuits.

BACKGROUND OF THE INVENTION

A number of metrology tools are now available for performing optical measurements on semiconductors. Such tools can include spectroscopic reflectometers and spectroscopic ellipsometers. Examples of such tools can be found in U.S. Pat. Nos. 5,608,526 and 6,278,519, both incorporated by reference. Such tools typically include a broadband light source for generating a probe beam that is directed to reflect off the sample. Changes in intensity or polarization state of the beam as a function wavelength are monitored to yield information about the sample.

Given the continuing shrinking feature size of semiconductor circuits, it is desirable to design the illumination system to provide a tightly focused probe beam to form a small spot on the sample surface. Several focusing assemblies have been developed for this purpose. These focusing assemblies can be formed from refractive or reflective elements or a combination of each (cadiatropic assemblies).

For patterned samples, such as integrated circuits, the metrology instrument must measure within small test pads [i.e. often less than 50 microns wide] surrounded by a completely different material or film stack. The generation of adequate and meaningful contrast can be as important as resolution. Some of the difficulties in practice are:

(a) The optics must accommodate ever-smaller feature size [critical dimension] and tighter position [overlay] requirements, for specific materials.
(b) The optics must precisely locate the test feature boundaries, since any light falling on the surrounding features and collected by the detector can cause measurement error.
(c) The optics between the source and detector must minimize the radiation falling on or detected from areas outside the smallest measurable test feature. This condition must be achieved over the instrument's entire wavelength range.

In such systems, it is important to understand and control the range of light illumination and collection angles. The sine of the maximum illumination half angle is commonly referred to as the illuminator numerical aperture, or $NA_I$. The sine of the maximum collection half angle is commonly referred to as the collector numerical aperture, or $NA_C$. The numerical aperture of each branch of the illumination system is set by the smallest or limiting aperture in that branch. The limiting aperture can be a separate physical element or be part of the focusing system (lens assembly) or other optical element.

The most common practice in the art is to select $NA_I = NA_C$ (typical microscope systems are set up this way). With this selection (equal angular ranges for illumination and collection systems) the collection optics only lightly apodizes the reflected probe beam and the system has high throughput. A significant shortcoming of this arrangement is reduced image contrast for small features; e.g. image contrast is inversely proportional to object spatial frequency and, although the imaging system can provide high contrast images of large features, the image contrast of small features is degraded.

It is another common practice to set $NA_I > NA_C$ and even $NA_I >> NA_C$. Note that the spherical aberration and the resolution of the collection optics are proportional to $NA_C$ while the system throughput is proportional to $NA_C^2$. Decreasing $NA_C$ is advantageous since it reduces aperture dependent aberrations, e.g. spherical aberration. However, this reduction in aberrations comes at the cost of reduced throughput and degraded resolution. Reducing $NA_C$ has the further disadvantage that the collection aperture now heavily clips the reflected probe beam; this produces additional measurement error due to aperture dependent scatter and diffractive effects.

Neither of the conventional practices is completely satisfactory for small-spot optical spectroscopic measurement systems.

SUMMARY OF THE INVENTION

The subject of this invention is a family of optical designs for a metrology system wherein the beam-control apertures are selected and arranged such that the relative numerical aperture, $NA_R = NA_I/NA_C < 1$. Tailoring the partial coherence of the optical system using beam-controlling apertures in this manner enhances system performance by improving contrast and minimizing edge effects during measurements. This family of optical designs is applicable to a large class of broadband optical instruments commonly utilized in wafer metrology employing, spectrophotometry, spectroscopic reflectometry, spectroscopic ellipsometry and spectroscopic scatterometry techniques.

DETAILED DESCRIPTION OF THE PREFERRED EMBODIMENTS

As discussed above, the common practice in the art is to design instruments wherein the relative numerical aperture, $NA_R = NA_I/NA_C \geq 1$. The $NA_R$ is the ratio of the angular acceptance of the illuminator to the angular acceptance of collection optics, and is a direct measure of the partial coherence of the system; e.g. $NA_R = 0$, implies fully coherent illumination, $NA_R >> 1$ implies incoherent illumination. The subject invention is particularly useful for a family of optical designs for broadband optical systems wherein the beam-control apertures are selected such that $NA_R < 1$. The optical designs are applicable to a large class of broadband optical instruments commonly utilized in wafer metrology employing, spectrophotometry, spectroscopic reflectometry, spectroscopic ellipsometry and including spectroscopic scatterometry techniques. The benefits of the subject invention are not limited to broadband systems but are also applicable to inspection devices that use incoherent light to illuminate the sample.

Characteristically, these optical systems include an illumination system, a sample and a detection system. The detection system is arranged to intercept a portion of the illumination upon reflection from and interaction with the sample and generate output signals in response to the intercepted illumination.

As will become evident from the teachings of this patent, optical designs with beam-control apertures configured such that $0 \leq NA_R \leq 1$, offer several advantages heretofore unrecognized in the prior art; most importantly, improved sensitivity and accuracy for small-spot, broadband, multi-wavelength optical metrology systems.

Figure 1:
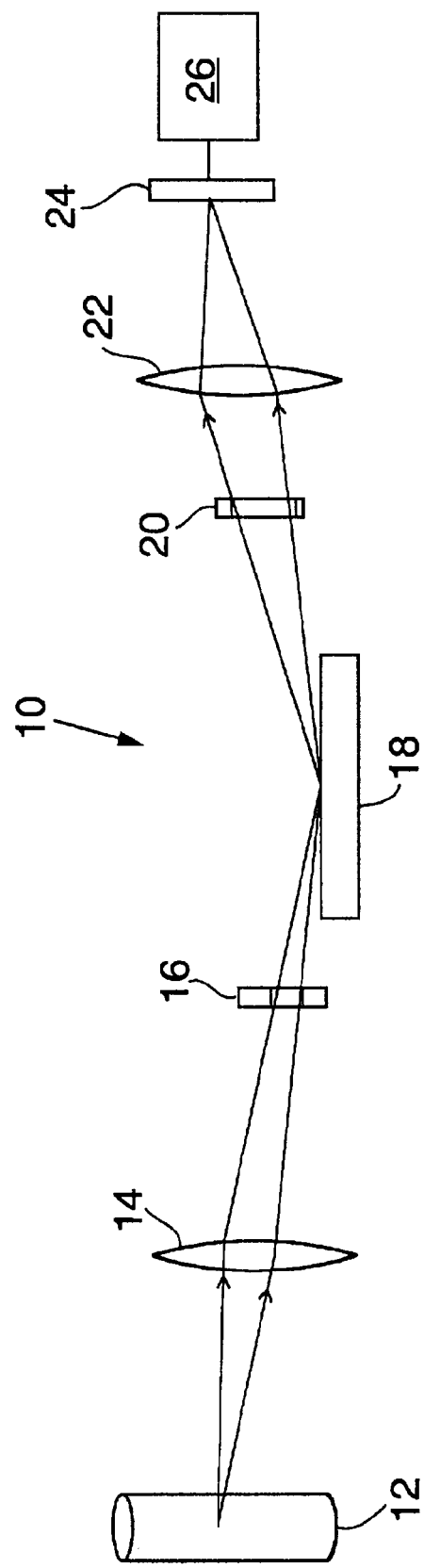
FIG. 1 is a schematic diagram of a generalized optical wafer metrology instrument.

FIG. 1 is a highly schematic rendering of a preferred embodiment of the invention 10. A highly simplified optical representation has been used to reduce the complexity of the figure. Individual optical components are used to represent functional elements that may be quite complex; for example, a lens represents an optical system for collecting and focusing light—the physical embodiment of the optical system may employ multiple lenses in multiple groups.

The system includes an incoherent light source 12. In the preferred embodiment, light source 12 emits broadband illumination to define a polychromatic probe beam of radiation. Current commercial broadband measurement systems of the assignee include both visible and UV capabilities. In such systems, it is possible to utilize two or more light sources in combination to provide a full spectral range. The scope of the subject invention is not limited to the particular range of wavelengths used.

A portion of the illumination is collected by the illuminator optical system 14 and is focused through illuminator aperture 16. Aperture 16 serves to limit the angular range of the illumination system, expressed as the illuminator numerical aperture, $NA_I$. As noted above, the aperture 16 need not be a separate optical element, but could, for example, be part of the focusing optical system 14.

The transmitted light is brought to a focus on the surface of sample 18. In the preferred commercial embodiments, the spot size of the beam can be on the order of tens of microns in diameter.

The focused radiation interacts with and reflects from sample 18 and is transmitted through collection optics aperture 20 that limits the angular acceptance of the collection system to a collection numerical aperture $NA_C$. The transmitted illumination is collected or collimated by collection optical system 22. Similar to the illumination side, the numerical aperture of the collection side can be governed by the diameter and radius of the collecting optics rather than through use of a separate aperture 20 as shown.

The collimated light is directed to detector system 24 that generates output signals in response to the incident illumination. In the preferred embodiment, the detector system includes a spectrometer which generates an output as a function of wavelength. An ellipsometer systems would typically also include an analyzer that can be defined by a rotating polarizer or compensator. In either case, the output signals are supplied to a processor which can analyze characteristics of the sample based on the measurements. The general operation of systems such as reflectometers and ellipsometers to measure and analyze reflected light is well known to those skilled in the art and need not be discussed herein.

System 10 is a generalized optical system than can include a plurality of spectroscopic wafer metrology tools, used individually or in combination to measure the characteristics of a sample, including spectrophotometers, reflectometers, polarized beam reflectometers, spectroscopic ellispometers, optical CD and overlay metrology tools and related incoherent, single-wavelength instruments.

Note that in a given embodiment it may be desirable to fix the locations and sizes of the illumination and collection apertures to optimize the optical system for a given range of parameters and measurements. In another configuration is may be desirable that the numerical apertures of the illumination and collection branches be variable so that they may assume a range of selectably controlled values. In this latter configuration the metrology system may be dynamically optimized to improve performance over a broad range of parameters and measurements.

As illustrated schematically in FIG. 1, $NA_C > NA_I$, e.g. the angular range of the collection system is larger than that of the illumination system and the relative numerical aperture, $NA_R \equiv NA_C/NA_I$, <1. This configuration, e.g. $NA_R < 1$, of the metrology system achieves significant advantages heretofore unrecognized in the prior art. The $NA_R$ can be selected to increase system resolution, improve edge contrast, balance both amplitude and phase distortion and correct for "errors" produced by optical fabrication, optical mounting and optical alignment.

Generally, the illuminator optical system overfills the illumination aperture and the aperture "clips" or apodizes the light. The aperture can provide several functions that are related to the degree of "clipping" or apodization of the beam.

If the illumination intensity varies strongly across the aperture, the uniformity of illumination at the sample may be improved by reducing the aperture diameter and $NA_I$. This has several effects. In the absence of significant diffraction, aperture dependent aberrations of the optical system are reduced and the uniformity of the illuminated spot is improved. The $NA_I$ is reduced so the partial coherence of the illumination is increased; this increases sensitivity to diffractive effects improving edge contrast. Of course, these benefits accrue at the expense of illumination intensity—with a reduced aperture less light strikes the sample surface. This reduces the signal; this may increase measurement time and reduce system throughput.

If the illumination at the aperture is highly uniform, the aperture may be configured to only weakly apodize the beam. In this case the dominant function of the aperture is to suppress stray or scattered light. Of course, this also limits the angular range of the illumination and increases the partial coherence of the illumination.

The collection optics aperture controls the angular range of the illumination that reaches the detector. As discussed above, it has been a common practice in the prior art to select the illumination and collection system apertures such that $NA_I > NA_C$ or even $NA_I >> NA_C$. In these arrangements, the illuminator aperture is of limited utility since it has negligible effect on the performance characteristic of the metrology system. Further, in these prior art systems, it is the collection optics aperture that dominates the metrology system optical performance setting the "effective" spot-size, resolution, partial coherence and throughput of the metrology system.

An arrangement in accordance with the subject invention, wherein $NA_C > NA_I$ ($NA_R \equiv NA_I/NA_C < 1$), offers superior control of the illumination and detection characteristics of the optical system. The illumination and collection apertures may be individually selected to optimize system performance. This has been unrecognized in the prior art.

For example, the illumination aperture may be selected to improve the uniformity of illumination. Selecting $NA_C > NA_I$ allows the collection system to detect illumination over a larger angular range. This increases the resolution of the collection optical system and improves collection efficiency for light diffracted out of the specularly reflected beam. Independent control of the spot size and collection "bandwidth" permits optimization of the system to increase the contrast of edge-like features at high spatial resolution. This is illustrated in FIG. 2.

Figure 2:
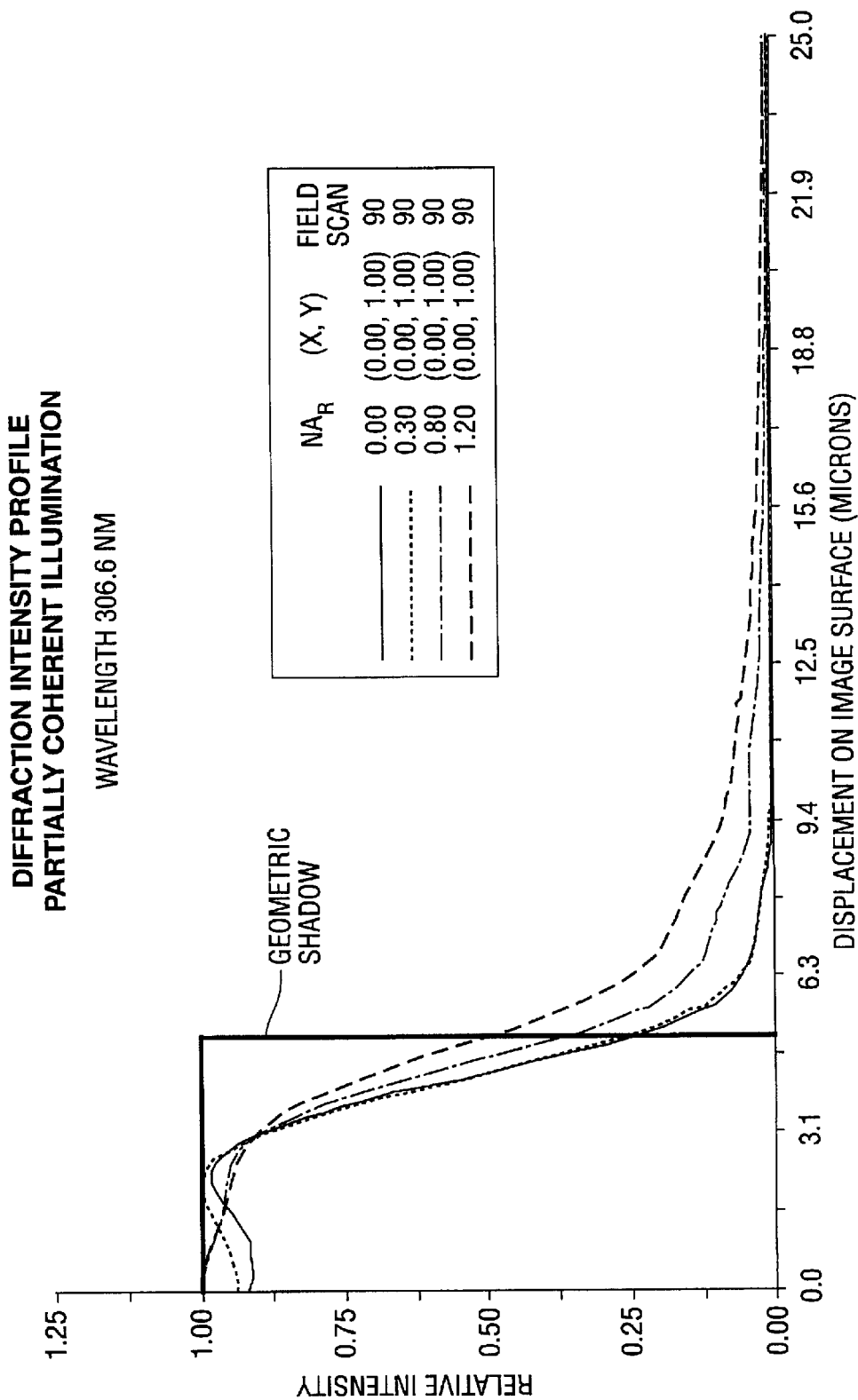
FIG. 2 is a theoretical plot of image contrast (intensity vs. position) for a 10 micron bar object for an optical system with a relative numerical aperture varying between $0 \leq NA_R \leq 1.2$.

FIG. 2 shows a model calculation of the diffracted intensity (in arbitrary units) as a function of distance (in microns) from a 10 µm wide bar object for an optical system with unit magnification. Distance is measured from image center. The geometrical footprint of the object is shown, for reference, at the image plane.

As can be appreciated, in an idealized measurement situation, the measured intensity will exhibit a sharp change as the edge of the beam spot moves off the bar object. However, diffraction effects will cause the measured intensity to fall off in a sloped fashion as the edge of the beam spot moves off the bar object. In FIG. 2, the diffracted intensity is computed for relative numerical apertures in the range between $0 < NA_R < 1.2$. As can be seen, as the $NA_R$ is reduced, the contrast and sharpness of the curve is increased. Significantly, a considerable amount of contrast improvement can be obtained by a relatively small reduction of $NA_R$, from the conventional 1.0 to 0.8. Of course, additional improvement in contrast can be obtained by reduced $NA_R$ even further. However, as noted above, reducing the illumination aperture reduces light levels reducing throughput. Therefore, it is believed that the $NA_R$ should be selected so that the desired improvements in contrast are balanced with the reduction in throughput. In initial experiments, it appears that $NA_R$ in the range of 0.5 to 0.9 would achieve that balance with a range of 0.7 to 0.9 being preferred.

Note that for $NA_R < 0.30$ the diffracted intensity approaches that predicted for fully coherent illumination, $NA_R = 0$ and the edge contrast is a maximum.

Figure 3A:
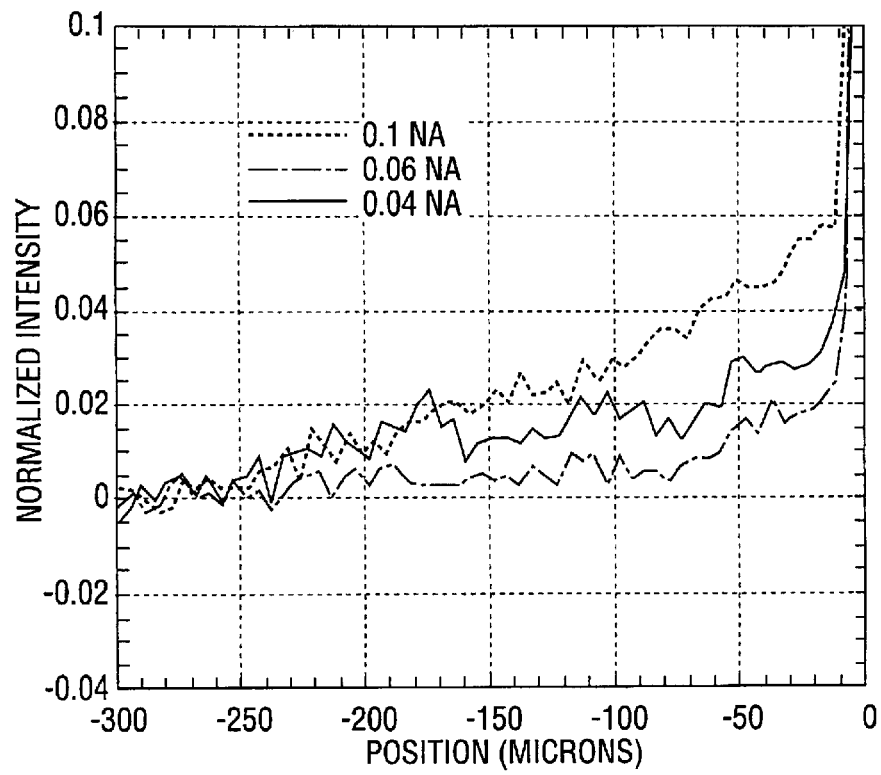
FIG. 3a illustrates the measured variation in reflected dc intensity measured by a spectrophotometer as a function of distance from a "step-edge" feature at different $NA_I$'s.
Figure 3B:
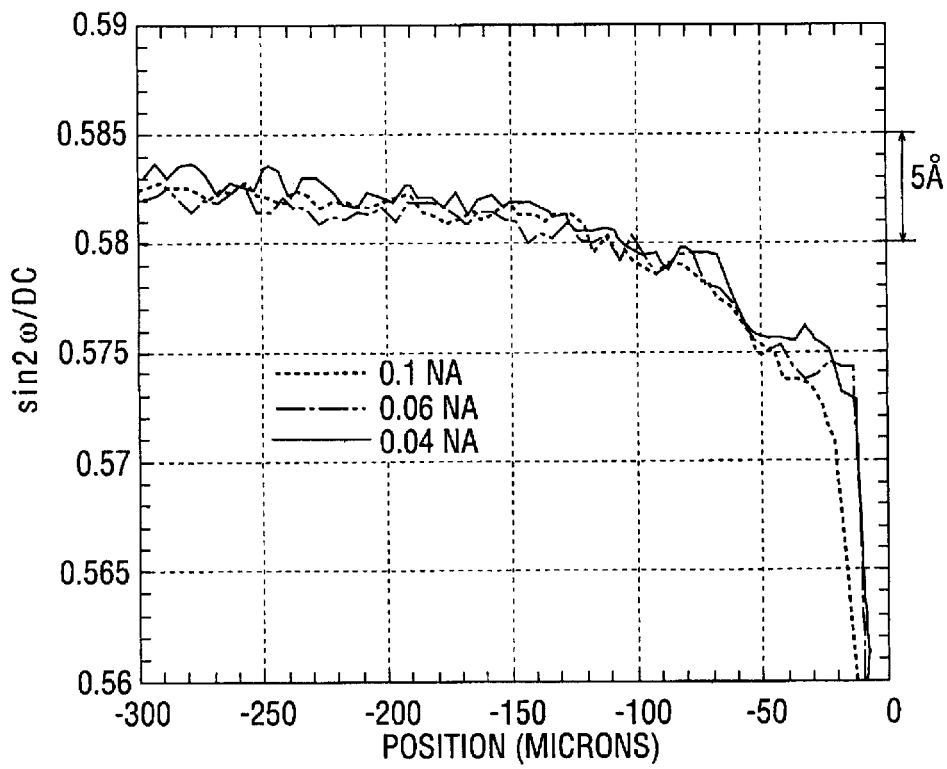
FIG. 3b illustrates the measured variation in a 2ω signal measured by a spectroscopic ellipsometer as a function of distance from a "step-edge" feature for different $NA_I$'s.

FIG. 3 illustrates actual measured variations in reflected intensity as a function of distance from a "step-edge" feature as a function of $NA_I$. The measurements were taken on a device similar to assignee's Opti-Probe. FIG. 3a illustrates dc signals obtained from the spectroscopic reflectometer. FIG. 3b shows a 2ω signal from a rotating compensator spectroscopic ellipsometry system. The dc signal of FIG. 3a is normalized to measurements obtained from a reference sample. The 2ω signal of FIG. 3b is normalized to the dc signal.

The x-axis of the Figures indicates the position of the measurement spot from the edge of a 500 Angstrom thick $SiO_2$ pad on a Si substrate that has a native (20 Angstrom) oxide layer. The pad is 600 microns wide and the illumination spot is 20 microns in diameter at 10% of peak intensity. $NA_C$ is 0.1 for each example. The measured response is shown for three different illumination apertures, $NA_I = 0.04$, 0.06 and 0.1 ($NA_R$ of 0.4, 0.6 and 1.0 respectively). The variation in signal as one approaches the edge (x=0) illustrates the effect of the surrounding material on the edge contrast. In particular, by reducing the illumination $NA_I$, one can obtain a much sharper edge on the measurement.

The significance can be best be appreciated from FIG. 3b where each major y-axis division corresponds to an "apparent" thickness change of 5 Angstroms. As can be seen, with an $NA_I$ of 0.1 ($NA_R$ of 1.0), the edge of the pad begins to dramatically effect the measurement at a location much farther away from the pad than when using a lower $NA_I$.

As discussed above, reducing $NA_I$ increases the partial coherence of the illumination and increases the sensitivity to edge effects. The data illustrate this phenomenon and show that sharper edges are obtained for both reflectivity (figure on left) and ellipsometry (figure on the right) as $NA_I$ is reduced.

While the subject invention has been described with reference to a preferred embodiment, various changes and modifications could be made therein, by one skilled in the art, without varying from the scope and spirit of the subject invention as defined by the appended claims

I claim:

1. A method for evaluating a sample with a optical wafer metrology tool employing an incoherent light source, illumination optics that collect a portion of the light from the source and illuminate the sample at a small-spot, the illumination interacting with and reflecting from the sample, collection optics that collect at least a fraction of the reflected illumination, a detection system generating output signals in response to the collected illumination and a processor for recording and analyzing the output signals, said method comprising:

limiting the angular range of the illumination striking the sample to an illumination numerical aperture, $NA_I$;

limiting the angular variation of the fraction of the reflected radiation collected by the collection optics to a collection numerical aperture, $NA_C$;

constraining the above described angular limitations to configurations where $NA_C > NA_I$, whereby the relative numerical aperture $NA_R \equiv NA_I/NA_C$ assumes a value less than 1.

2. The method of claim 1 where $NA_R$ is less than 0.9.

3. The method of claim 1 where $NA_R$ is less than 0.8.

4. The arrangement of claim 1 where $0.50 \leq NA_R \leq 0.90$.

5. The arrangement of claim 1 where $0.70 \leq NA_R \leq 0.90$.

6. The arrangement of either claim 4 or 5 wherein the $NA_R$ is adjustable.

7. The method of any of claims 1 to 5 wherein the light source is a broadband light source and the optical metrology tool employs at least one metrology system selected from the group consisting of spectroscopic reflectometers, polarized beam spectroscopic reflectometers, spectroscopic ellipsometers and spectroscopic scatterometers.

8. An arrangement of an optical metrology tool for evaluating a sample with light, including an incoherent light source, illumination optics that collect a portion of the light from the source and illuminate the sample at a small-spot, the illumination interacting with and reflecting from the sample, collection optics that collect at least a fraction of the reflected illumination, a detection system generating output signals in response to the collected illumination and a processor for recording and analyzing the output signals, said arrangement including:

means for limiting the angular range of the illumination striking the sample to an illumination numerical aperture, $NA_I$;

means for limiting the angular variation of the fraction of the reflected radiation collected by the collection optics to a collection numerical aperture, $NA_C$;

selecting $NA_C$ and $NA_I$ such that $NA_C > NA_I$, whereby the relative numerical aperture $NA_R \equiv NA_I/NA_C$ assumes a value less than 1.

9. The arrangement of claim 8 where $NA_R$ is less than 0.9.

10. The arrangement of claim 8 where $NA_R$ is less than 0.8.

11. The arrangement of claim 8 where $0.50 \leq NA_R \leq 0.90$.

12. The arrangement of claim 8 where $0.70 \leq NA_R \leq 0.90$.

13. The arrangement of either claims 11 or 12 wherein the $NA_R$ is adjustable.

14. The arrangement of any of claims 8 to 12 wherein the light source is a broadband light source and the optical metrology tool employs at least one metrology system selected from the group consisting of spectroscopic reflectometers, polarized beam spectroscopic reflectometers, spectroscopic ellipsometers and spectroscopic scatterometers.

15. An apparatus for evaluating a sample with light including an incoherent light source, illumination optics that collect a portion of the light from the source and illuminate the sample at a small-spot, the illumination interacting with and reflecting from the sample, collection optics that collect at least a fraction of the reflected illumination, a detection system generating output signals in response to the collected illumination and a processor for recording and analyzing the output signals, said apparatus further including:

a first beam-limiting aperture for limiting the angular range of the illumination striking the sample to an illumination numerical aperture, $NA_I$;

a second beam-limiting aperture for limiting the angular variation of the fraction of the reflected radiation collected by the collection optics to a collection numerical aperture, $NA_C$;

said first and second apertures configured so that $NA_C > NA_I$, whereby the relative numerical aperture $NA_R \equiv NA_I/NA_C$ assumes a value less than 1.

16. The apparatus of claim 15 where $NA_R$ is less than 0.9.

17. The apparatus of claim 15 where $NA_R$ is less than 0.8.

18. The apparatus of claim 15 where $0.50 \leq NA_R \leq 0.90$.

19. The apparatus of claim 15 where $0.70 \leq NA_R \leq 0.90$.

20. The apparatus of claims 18 or 19 wherein the $NA_R$ is adjustable.

21. The apparatus of an of claims 15 to 19 wherein the light source is a broadband light source and the optical metrology tool employs at least one metrology system selected from the group consisting of spectroscopic reflectometers, polarized beam spectroscopic reflectometers, spectroscopic ellipsometers and spectroscopic scatterometers.

22. The apparatus of claim 21 wherein the metrology tool employs a plurality of metrology systems selected from the group consisting of reflectometers, polarized beam reflectometers, ellipsometers, scatterometers, optical CD metrology tools, spectroscopic reflectometers, polarized beam spectroscopic reflectometers, spectroscopic ellipsometers, spectroscopic scatterometers and spectroscopic optical CD metrology tools, and the processor analyzes the detector outputs either individually or in combination to evaluate the sample.

23. An apparatus for evaluating characteristics of a sample comprising:

a broad band light source for generating a polychromatic probe beam of radiation;

an optical element for focusing the probe beam to a small spot on the surface of the sample;

collection optics for gathering the reflected probe beam radiation;

a detector system for measuring changes in the probe beam due to interaction with the sample and generating output signals in response thereto;

a processor for evaluating characteristics of the sample based on the output signals and wherein the illumination path is configured to have a numerical aperture ($NA_I$) less than the numerical aperture of the collection path ($NA_C$) whereby the relative numerical aperture $NA_R \equiv NA_I/NA_C$ assumes a value less than 1.

24. The apparatus of claim 23 where $NA_R$ is less than 0.9.

25. The apparatus of claim 23 where $NA_R$ is less than 0.8.

26. The apparatus of claim 23 where $0.50 \leq NA_R \leq 0.90$.

27. The apparatus of claim 23 where $0.70 \leq NA_R \leq 0.90$.

28. The apparatus of claims 26 or 27 wherein the $NA_R$ is adjustable.

* * * * *